United States Patent [19]

Ouvrard

[11] 4,023,397
[45] May 17, 1977

[54] METHOD AND APPARATUS FOR THE CONTINUOUS AUTOMATIC ANALYSIS OF THE FILTERABILITY POINT OF LIQUIDS, PARTICULARLY DOPED DIESEL OIL

[75] Inventor: Paul Ouvrard, Saint Nazaire, France

[73] Assignee: Societe Anonyme Dite: Antar Petroles de l'Atlantique, Paris, France

[22] Filed: Mar. 4, 1976

[21] Appl. No.: 663,775

Related U.S. Application Data

[63] Continuation-in-part of Ser. No. 505,645, Sept. 13, 1974, Pat. No. 3,945,243.

[30] Foreign Application Priority Data

Sept. 19, 1973 France ............................. 73.33670

[52] U.S. Cl. ................................. 73/17 R; 73/61.4
[51] Int. Cl.² ....................................... G01N 25/04
[58] Field of Search ........................... 73/17 R, 61.4

[56] References Cited

UNITED STATES PATENTS

| | | | |
|---|---|---|---|
| 2,591,084 | 4/1952 | Martin | 73/17 R |
| 2,750,433 | 6/1956 | Tourneau et al. | 73/17 R X |
| 2,997,874 | 8/1961 | Billaris et al. | 73/17 R X |
| 3,143,876 | 8/1964 | Wallgren | 73/17 R |
| 3,213,668 | 10/1965 | Thompson | 73/17 R |
| 3,577,765 | 5/1971 | Bertoglio et al. | 73/17 R |
| 3,872,710 | 3/1975 | Louvel | 73/17 R |

Primary Examiner—Richard C. Queisser
Assistant Examiner—Joseph W. Roskos
Attorney, Agent, or Firm—Hammond & Littell

[57] ABSTRACT

A method and apparatus for the continuous automatic measuring of the filterability threshold temperature of a liquid such as a doped diesel oil comprising passing the doped diesel oil through a measuring circuit surrounded by a cooling liquid at a constant flow rate, providing a crystal retaining means beyond the cooled part of said measuring circuit, measuring the pressure differential before and immediately after said crystal retaining means, and providing resistance heating to said measuring circuit when the measured pressure differential exceeds a predetermined value and continuously measuring the temperature of said liquid immediately down stream of said crystal retaining means. The switch of the device is actuated in response to the pressure differential increasing beyond a predetermined level which is caused by a build-up of microcrystals, for turning on the resistance heating circuit and melting the microcrystals. The heating circuit is then automatically turned off when all the microcrystals have melted, by the corresponding decrease in pressure differential in the measuring circuit in response to which the device actuates the switch once again back to its initial position.

11 Claims, 7 Drawing Figures

FIG.4

METHOD AND APPARATUS FOR THE CONTINUOUS AUTOMATIC ANALYSIS OF THE FILTERABILITY POINT OF LIQUIDS, PARTICULARLY DOPED DIESEL OIL

REFERENCE TO A PRIOR APPLICATION

This application is a continuation-in-part of my copending U.S. Pat. application Ser. No. 505,645, filed Sept. 13, 1974, now U.S. Pat. No. 3,945,243.

RELATED ART

The present invention relates to a method and device for the continuous automatic analysis of the "filterability point" of liquid substances, particularly doped diesel oil in the process of manufacture.

In the present description the term "filterability point" generally defines the flowability of a liquid substance as its temperature drops.

Diesel oil intended for use in Diesel engines must pass a particular test, called the "filterability point test." The filterability point is the point at which the filters are clogged. The test carried out on diesel oil is, therefore, intended to determine the value of the temperature below which the appearance of microcrystals of paraffin in the midst of the liquid is capable of blocking or clogging the filters protecting the injectors.

Up to now this analysis has been carried out in the laboratory with the aid of equipment whose modus operandi will be given in brief hereinafter with reference to FIG. 1 of the accompanying drawings.

The substance 1 to be analyzed contained in the measuring test tube 2 is immersed in a cooling bath 3 whose temperature is maintained at a value sufficiently below the assumed filterability point.

The substance 1 passes into a tube 4 connected to a chamber 5 and is filtered by a filter 6 having a standardized mesh and positioned inside the chamber 5. Periodically a partial vacuum of constant magnitude is applied to the upper part of the chamber 5 until 20 cubic centimeters of liquid have passed through the filter. The manometer 10 monitors the value of the partial vacuum applied. A graduation 8 located along the suction tube enables accurate measurement of volumetric displacement.

By means of the two-way valve 9 located downstream of the filtering chamber 5 during suction, when sufficient of the substance 1 reaches the graduation 8 corresponding to a quantity of 20 cubic centimeters of liquid, the partial vacuum is then cut off by bringing the downstream end of the filtering chamber into communication with ambient air, thereby enabling the return of the substance displaced back into the test tube 2.

In the filtering chamber 5, downstream of the filter itself, a device 7 for measuring the temperature is positioned. The principle of measurement consists in marking the temperature of the filtering diesel oil above which the displacement of 20 cubic centimeters requires more than one minute.

In this analysis procedure, the energy for filtration (in this case, the value of the partial vacuum drawing up the liquid) is constant and the flow rate is variable. In fact, the displacement time for 20 cubic centimeters of liquid 1 is a few seconds so long as the diesel oil is at a temperature sufficiently higher than the filterability point. However, this time increases rapidly as temperature approaches the filterability point since the clogging of the filter reduces the effective section of passage therethrough.

The equipment is either controlled manually by an operator or there are also automated set-ups in which the successive sequences of suction and measurement of displacement time are controlled automatically. However, these techniques which are very useful in the laboratory cannot be used on production sites for continuous quality control at all times.

An automatic device for determining the filterability point is described in U.S. Pat. No. 3,872,710. This patent relates to a system continuously measuring the filterability point or index. The measure is made with a standardized pressure at the inlet of the tube means including a chamber which is divided by filtering means. The temperature of the fluid as it passes through the filter is controlled to remain at a well-defined value, the flow rate corresponding to the filterability point F. Said temperature then oscillates round the filterability point F according to sequences controlled by a rate sensor. In this method the control system is done at a well defined value of the flow rate before and after the filter. The patent device comprises a liquid distributor with a standardized pressure and a detector sensing the rate drop in the flow meter on the filter.

In the parent application Ser. No. 505,645, another method of automatically determining the filterability point is described which comprises a simplified measuring circuit, which is constituted by a capillary tube acting both as a filter means and a heating resistor. This capillary tube avoids in the circuit the presence of a measuring chamber provided with a standardized meshed filter and with heating means. Furthermore, the cooling of the capillary tube is easier than the cooling of the entire volume of the measuring chamber. In particular, this patent describes and claims an apparatus for the continuous automatic measure of the filterability threshold temperature of a liquid substance comprising a block made of a metal having a high thermal inertia, said block having an external surface and a closed recess therein, a cooling liquid substantially filling said recess, said cooling liquid having a freezing temperature substantially lower than the average filterability threshold temperature of the type of liquid to be analyzed, cooling means on said external surface of said block adapted to cool said block, an electrically conductive metal capillary tube immersed in said cooling liquid and having an inlet end and an outlet end emerging from said block, said tube being electrically insulated from said block, pump means for delivering the liquid to be analyzed to said tube at a constant volume flow rate, electrical connecting means to connect both ends of said tube with the terminals of an electric power supply respectively, switch means interposed on one of said electrical connecting means, pressure responsive means in connection with said switch means whereby said electric power is supplied to said electrically conductive metal capillary tube when the difference between the inlet pressure and outlet pressure of said capillary tube exceeds a first predetermined value and suspends said supply of electric power when said pressure difference reaches a second predetermined value lower than said first value, thermosensitive means adapted to measure the temperature of the liquid to be analyzed in the outlet end of said capillary tube and means for recording the temperature measured by said thermosensitive means.

This device is especially adapted to be used in a large field of applications.

(1) It is especially adapted to the control of products having crystallizations of the "pasty" type contrary to the devices adapted to the analysis of pure products such as paraxylene, benzene, which have "clean" crystallization. The difference between the crystallizations of the pasty and the clean types is that the pasty crystallization is progressive, whereas the clean crystallization, which occurs mostly in aromatic compounds, presents a phenomenon preceding the crystallization itself and corresponding to the random under cooling.

(2) The high response rate of the device provides an easy integration in control loops of manufacturing units for a memorization with a low time constant of the filterability limiting temperature information.

The accuracy of the above analysis was found to be excellent when analyzing conventional diesel oils. However, most raw oils or diesel oils coming from distillation are improved by the addition of "dopes" in order to improve their ability to resist cold temperatures and more particularly to lower their limit temperature of filterability or filterability point. Unfortunately, with the above analyzer the diesel oils after doping retain essentially the same filterability index as before doping.

OBJECTS OF THE INVENTION

An object of the present invention is the development of a method and apparatus for the continuous automatic measuring of the filterability threshold temperature of a liquid such as a doped diesel oil by separating the functions of cooling the oil and producing a pressure differential.

Another object of the present invention is the development of apparatus for the continuous automatic measure of the filterability threshold temperature of a liquid substance comprising a container for a cooling liquid, a cooling liquid substantially filling said container, said cooling liquid having a freezing temperature substantially lower then the average filterability threshold temperature of the type of liquid to be analyzed, cooling means adapted to cool said cooling liquid, an electrically conductive metal tube immersed in said cooling liquid and having an inlet end and an outlet end emerging from said cooling liquid, said tube being electrically insulated, pump means for delivering the liquid to be analyzed to the inlet of said tube at a constant volume flow rate, a crystal retaining means at the outlet end of said tube emerging from said cooling liquid, electrical connecting means to connect both ends of said tube with the terminals of an electric power supply, respectively, switch means interposed on one of said electrical connecting means, pressure responsive means in connection with said switch means whereby said electric power is supplied to said electrically conductive metal tube when the difference between the pressure measured just before said crystal retaining means and the pressure measured just beyond said crystal retaining means exceeds a first predetermined value and suspends said supply of electric power when said pressure difference reaches a second predetermined value lower than said first value, thermosensitive means adapted to measure the temperature of the liquid to be analyzed just beyond said crystal retaining means, and means for recording the temperature measured by said thermosensitive means.

A further object of the present invention is the development of a process for the continuous automatic measure of the filterability threshold temperature of a liquid substance consisting essentially of the steps of pumping a liquid substance to be analyzed at a constant volume flow rate through an electrically conductive metal tube immersed in a cooling liquid having a freezing temperature substantially lower than the average filterability threshold temperature of said liquid substance to be analyzed, said metal tube being electrically insulated, passing said liquid substance from said tube through a crystal retaining means situated beyond said cooling liquid, measuring the pressure differential between both sides of said crystal retaining means, applying a supply of electrical power through said electrically conductive metal tube when the measured pressure differential exceeds a predetermined value, whereby said liquid substance is heated, and constantly measuring the temperature of said liquid substance at the outlet side of said crystal retaining means.

These and other objects of the invention will become more apparent as the description thereof proceeds.

THE DRAWINGS

DESCRIPTION OF THE INVENTION

Figure 1:
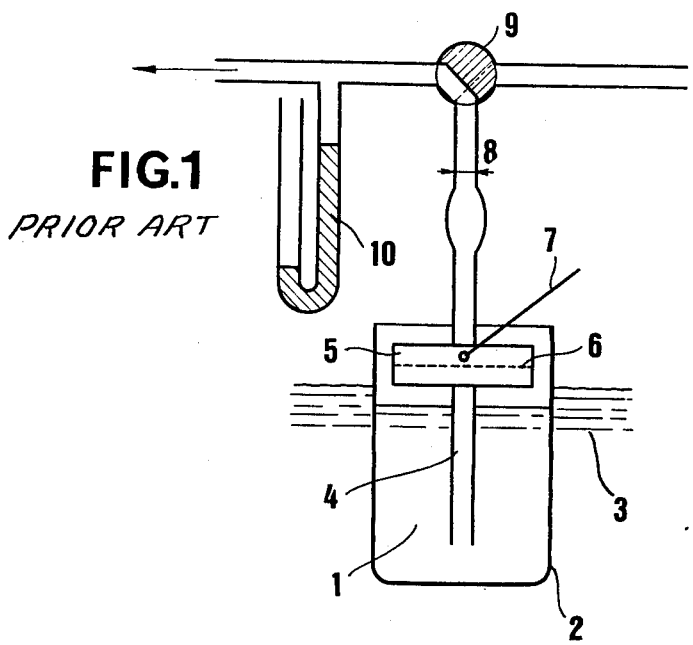
FIG. 1 shows a prior art device.
Figure 3:
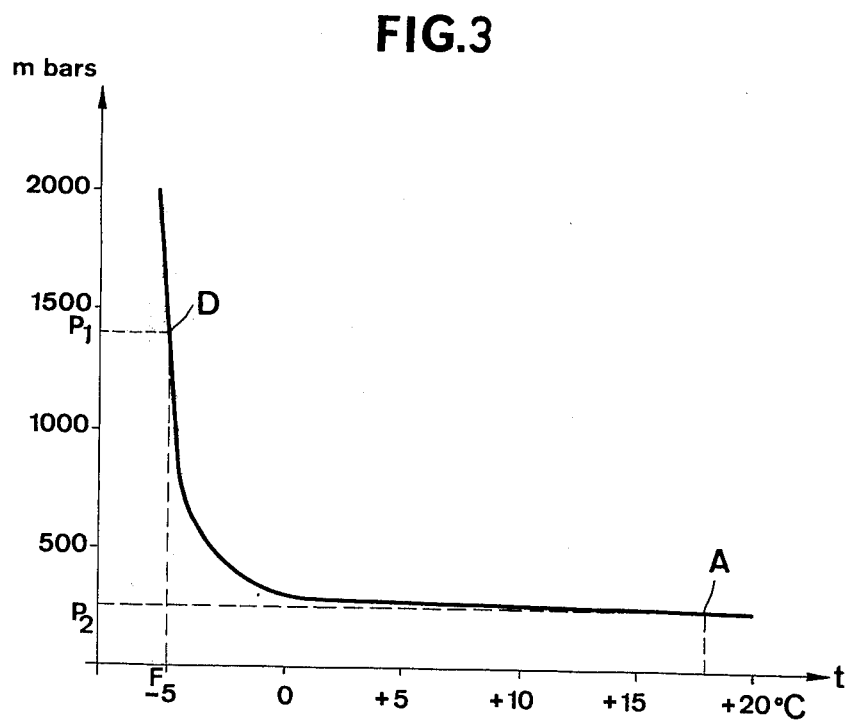
FIG. 3 is a graph showing the temperature-pressure drop relationship.

The difficulties of the accuracy of my prior art device for automatic measuring of the filterability point of a doped diesel oil is apparently due to the fact that in the measuring circuit, the capillary tube had simultaneously the two main functions: cooling and production of the pressure drop.

I have now discovered an apparatus for the continuous automatic measure of the filterability threshold temperature of a liquid substance comprising a container for a cooling liquid, a cooling liquid substantially filling said container, said cooling liquid having a freezing temperature substantially lower than the average filterability threshold temperature of the type of liquid to be analyzed, cooling means adapted to cool said cooling liquid, an electrically conductive metal tube immersed in said cooling liquid and having an inlet end and an outlet end emerging from said cooling liquid, said tube being electrically insulated, pump means for delivering the liquid to be analyzed to the inlet of said tube at a constant volume flow rate, a crystal retaining means at the outlet end of said tube emerging from said cooling liquid, electrical connecting means to connect both ends of said tube with the terminals of an electric power supply, respectively, switch means interposed on one of said electrical connecting means, pressure responsive means in connection with said switch means whereby said electric power is supplied to said electrically conductive metal tube when the difference between the pressure measured just before said cyrstal retaining means and the pressure measured just beyond said crystal retaining means exceeds a first predetermined value and suspends said supply of electric power when said pressure difference reaches a second predetermined value lower than said first tube, thermosensitive means adapted to measure the temperature of the liquid to be analyzed just beyond said crystal retaining means, and means for recording the temperature measured by said thermosensitive means; as well as a process for the continuous automatic measure of the filterability threshold temperature of a liquid substance consisting essentially of the steps of pumping a liquid substance to be analyzed at a constant volume flow rate through an electrically conductive metal tube immersed in a cooling liquid having a freezing temperature substantially lower than the average filterability threshold temperature of said liquid substance to be analyzed, said metal tube being electrically insulated, passing said liquid substance from said tube through a crystal retaining means situated beyond said cooling liquid, measuring the pressure differential between both sides of said crystal retaining means, applying a supply of electrical power through said electrically conductive metal tube when the measured pressure differential exceeds a predetermined value, whereby said liquid substance is heated, and constantly measuring the temperature of said liquid substance at the outlet side of said crystal retaining means.

It will be noted that in the present invention the two functions of cooling of the liquid to be measured and the production of the pressure drop are separated. The production of the pressure drop is accomplished by a means independent from the cooling circuit.

The sample to be analyzed is forced to circulate by the volumetric pump at constant flow through the cooling tubular circuit and, with the lowering of the temperature, the fluid flow which enters in solely liquid phase is progressively loaded with crystals and is then in the form of mixed phase (liquid/solid).

This circulation of mixed phase is then passed through a crystal retaining means, such as a filtering sieve or a capillary tube situated at the end of the cooling tubular circuit beyond the cooling area. The pressure drop differential is measured by a measurement of the pressure on each side of the crystal retaining means.

When the size of the crystals becomes sufficient, these latter accumulate on the crystal retaining means, such as a sieve, and engender a sensible increase of pressure drop (the flow being maintained constant). It should be noted that the sieve which produces the pressure drop can also be replaced by a piece of capillary tube or by any other crystal retaining means capable of offering a facility of different circulation, depending on the handling of a unique phase or a mixed phase.

The heating means of supplying an electric current to the tubular cooling circuit are controlled by a differential pressure responsive switching means. After the substance passes through this part of the circuit, the change of temperature is monitored from outside the housing by means of a thermosensitive element. The substance thus analyzed at the outlet of the measuring circuit is carried to a recovery circuit. The apparatus is fully automatic.

The operation of the prior art device of FIG. 1 has been described above.

Figure 2:
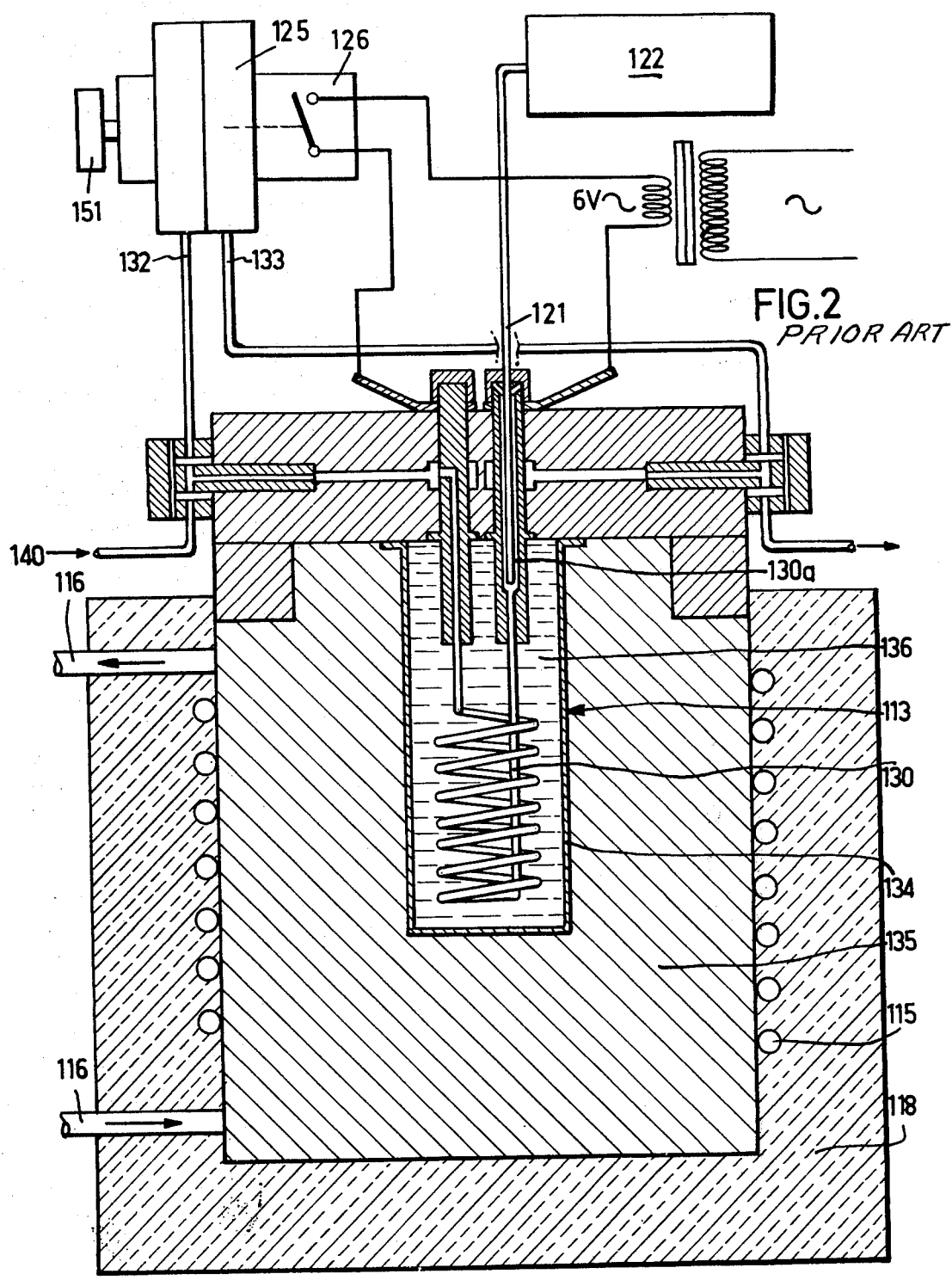
FIG. 2 shows the prior art device of the parent application.

The prior art filterability point analyzer apparatus shown in FIG. 2 comprises a measuring circuit including a stainless steel capillary tube 130.

The substance to be analyzed flows through the capillary tube 130 which passes through a well 113 which is constituted by a limited capacity cavity of about 80 cm$^3$ formed in a solid mass 135 of steel. The capillary tube has an outer diameter of 1.5 mm and an inner diameter of 1.2 mm and is formed so as to provide a rather substantial surface area in the measuring well. The tube 130 may, for example, be of helical configuration as illustrated in FIG. 2.

The measuring well 113 is lined with a Teflon sleeve 134 and filled with a non-freezing liquid 136.

The solid mass 135 of steel is cylindrical and is provided with a tubular evaporator 115 for a cooling unit connected at 116 and coiled thereabout.

The capillary tube 130 is about 100 cm long and has an electrical resistance of about 1 ohm. The inlet and outlet ends of the tube are mounted in bushings formed of insulating material and are connected across a switch 126 of a differential pressure responsive switching means 125 to a 6 true volt potential difference. The capillary tube 130 thus constitutes a heating element which consumes about 36 watts.

The capillary tube 130 has a widened portion 130a at the outlet of the measuring well, in order to receive a thermosensitive element 121 therein. The free end of the thermosensitive element 121 may be connected to a temperature recording device 122 and the busing between the portions of the element 121 located inside or outside the measuring circuit hermetically seals the tube 130.

The capillary tube 130 extends perpendicular to the widened portion 130a before communicating with the surambient atmosphere.

A constant flow rate of the substance to be analyzed is provided at the inlet 140 which enables the continuous circulation of the substance in the capillary tube 130. The continuous circulation in the analyzer apparatus causes a pressure drop in the circuit, then the progressive lowering of the temperature due to the cooling unit brings the substance circulating in the measuring circuit 130 to a temperature close to the value corresponding to the filterability point and causes the accumulation of microcrystals of paraffin along the inner wall of the capillary tube 130 and the rapid increase of the pressure drop in the measuring circuit 132–133.

An increase in the pressure drop to about 1400 millibars brings about the actuation of the differential pressure responsive means 125, i.e., the differential pressure responsive switch connected to the capillary tube 130 by means of inlet pressure tube 132 and outlet pressure tube 133 controls the starting of the reheating sequence applying a potential difference of 6 true volts to the terminals of the capillary tube 130. The capillary tube has a resistance of 1 ohm. The heating element constituted by the tube consumes 36 watts. The metal wall of the capillary tube 130 heats up and enables the efficient melting of the microcrystals which were deposited thereon.

The pressure drop due to the reduction of the effective cross-section caused by the crystallization of paraffin along the inner wall thereof, for a constant flow rate, rapidly returns to the initial value and in the proximity thereof, viz., near 700 millibars. The differential pressure switch 125 brings the heating sequence to an end, thereby enabling a new cooling sequence to begin.

The cooling is effected by means of the cooling bath 136 which is adapted to remove calories from the substance to be analyzed while providing a moment of thermal inertia sufficiently large so as to eliminate the inevitable variations in temperature resulting from the on-and-off operation of the cooling unit.

The elimination of variations is brought about by means of the solid mass 135 of steel. The specific heat of the steel is about one-eighth the specific heat of an aqueous solution but its density which is about seven times greater gives for an equivalent volume a moment of thermal inertia substantially equal to that of a large liquid bath.

The measuring well 113 is filled with a non-freezing liquid 136 with a view to ensuring that heat transfer between the low temperature source which is constituted by the metal mass 135 and the capillary tube 130 immersed in the measuring well.

The temperature of the non-freezing liquid is intermediary regulated in the course of the sequence by the periodic reheating of the capillary tube while the temperature of the solid mass 135 is maintained at a constant temperature of −25° C by the thermostat of the cooling unit.

The thermocouple 121 which measures the filterability point temperature remains at the outlet end of the capillary tube 130 and enables the continuous recording of the changes of the temperature between the minima representing the variations of the filterability point P.F. and the maxima representing the maximum temperature reached for ensuring the complete melting MP of the microcrystals.

Figure 4:
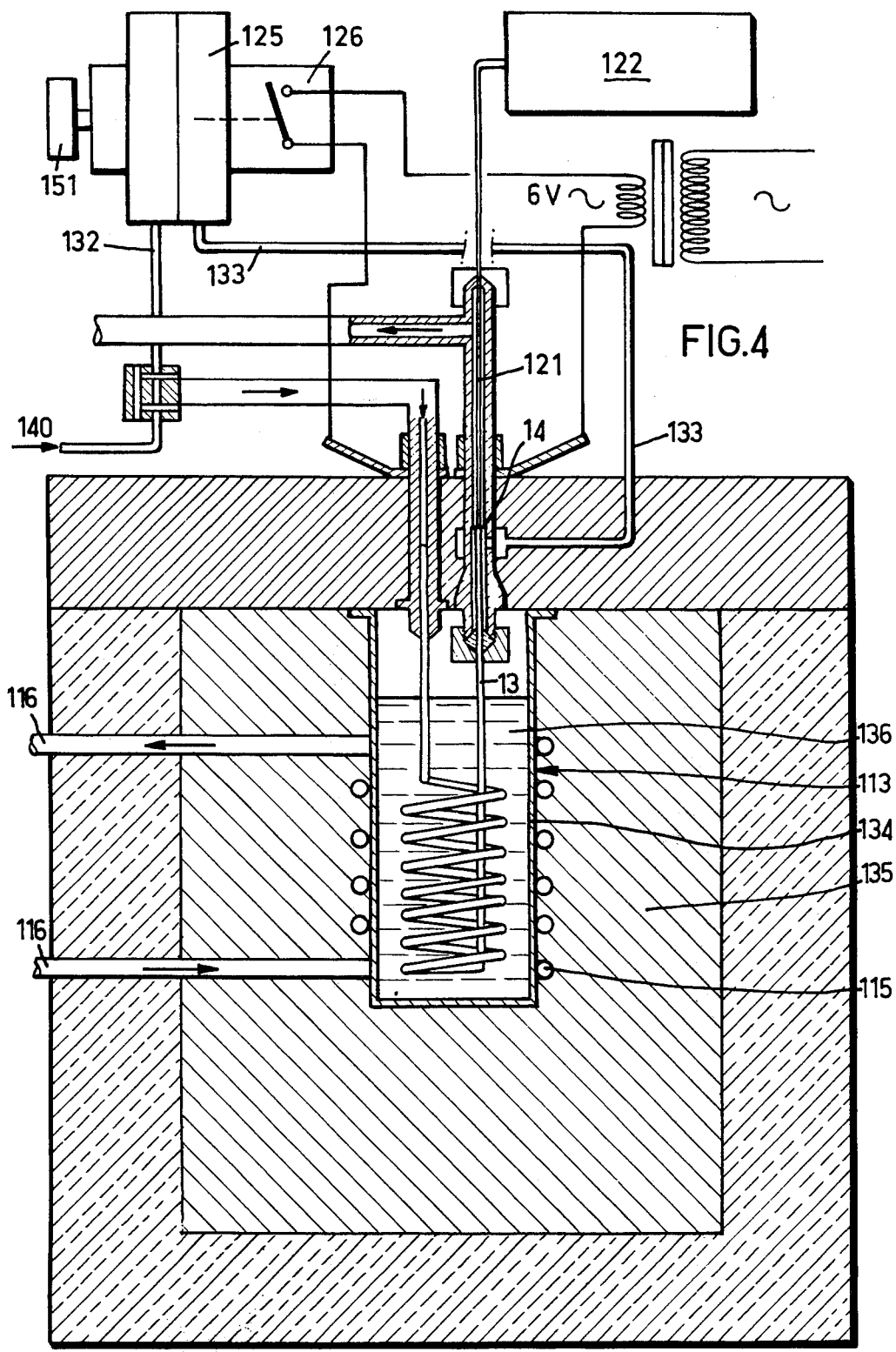
FIG. 4 is a schematic illustration of the apparatus of the invention.
Figure 5:
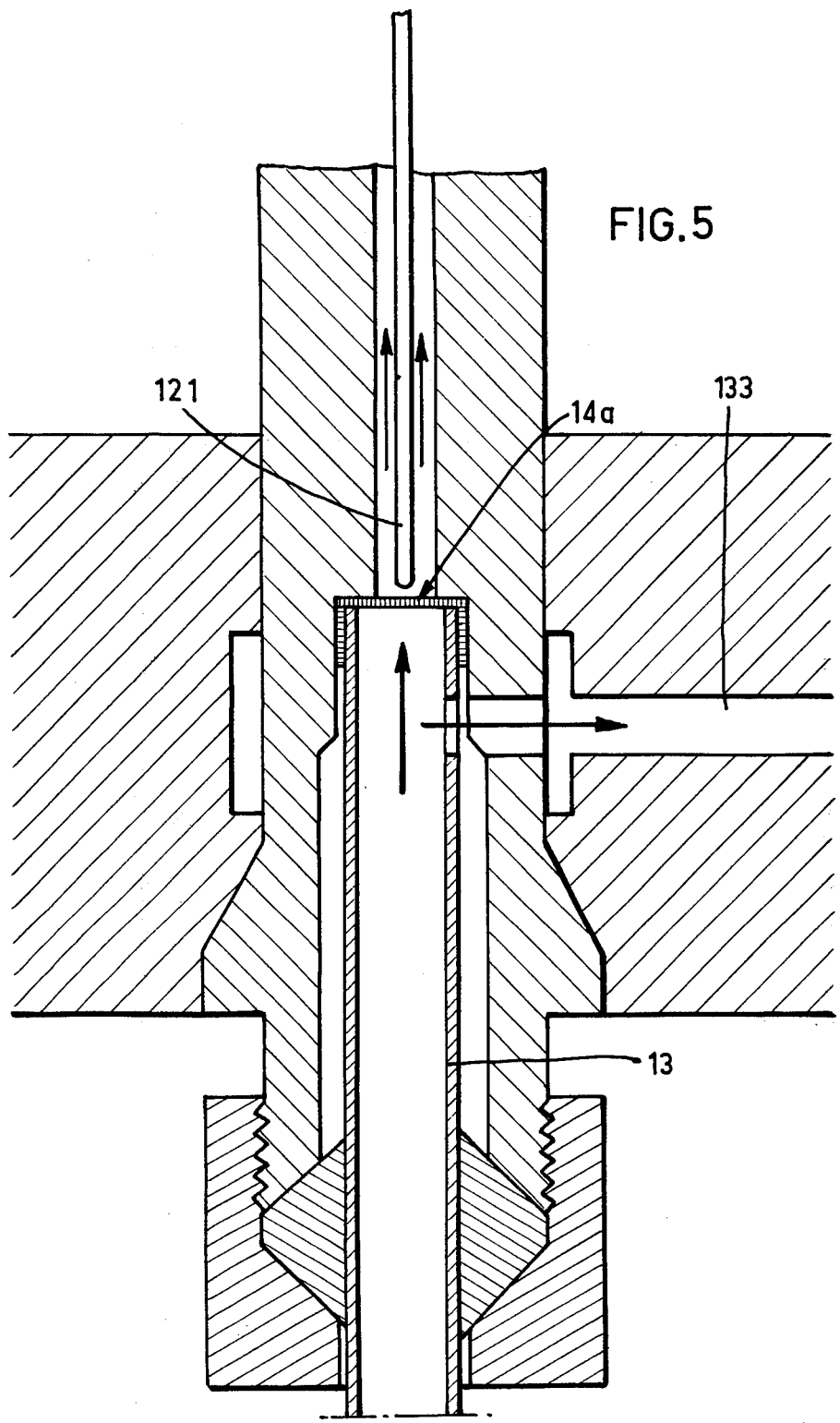
FIG. 5 is a schematic illustration of one type of crystal retaining means.
Figure 6:
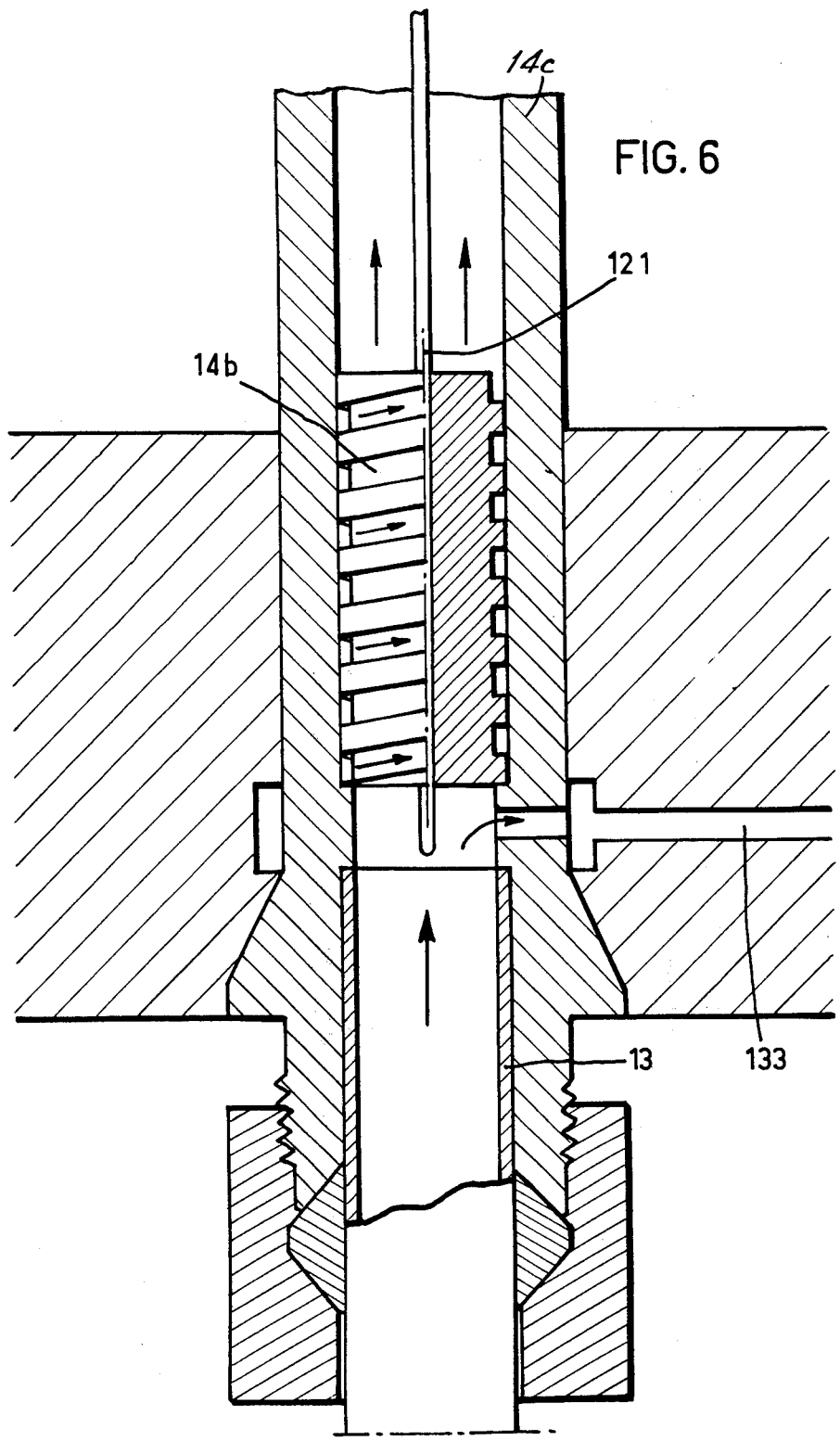
FIG. 6 is a schematic illustration of another type of crystal retaining means.

The apparatus of the present invention is illustrated by FIGS. 4 to 6. This apparatus has many features which are similar to the above discussed prior art device. These features have the same reference numerals.

The substance to be analyzed flows through an electrically conductive metal tube 13 which passes through an area of cavity 113 which is constituted by a limited capacity cavity of about 80 cm$^3$ formed in a solid mass 135 of steel. The metal tube is formed so as to provide a rather substantial surface area in the area of cavity 113. The tube 13 may, for example, be of helical configuration as illustrated in FIG. 4; however, other types of configurations may be employed.

The area of cavity 113 is lined with a Teflon sleeve 134 and filled with a non-freezing liquid 136. The solid mass 135 of steel is cylindrical and is provided with a tubular evaporator 115 for a cooling unit connected at 116 and coiled thereabout.

In place of the solid mass 135 of steel, another cold sink may be employed such as a large body of liquid.

The metal tube 13 is about 100 cm long and has an electrical resistance of about 0.05 ohm. The inlet and outlet ends of the tube are mounted in bushings formed of insulating material and are connected across a switch 126 of a differential pressure responsive switching means 125 to a 1.5 volt alternating current of 30 amperes. The tube 13 thus constitutes a heating element which consumes about 45 watts.

At the outlet end of the metal tube 13 above the surface of the cooling liquid 136 and the solid mass 135 of steel, a crystal retaining means 14 is mounted. As is shown in FIG. 5, an expanded view of the end of the metal tube 13, this crystal retaining means 14 is a sieve 14a. In the embodiment of FIG. 6, an expanded view of the end of the metal tube 13, this crystal retaining means 14 is a helicoid capillary 14b.

In this instance the pressure drop is provided by a helicoid path having a capillary cross-section. After flowing through the cooling tube 13, the liquid flows through this path which is constituted by a helicoidal throat (or groove) machined in a core included in the outlet connector of the product. This piece constitutes a confining means producing a pressure drop. The helicoid capillary in FIG. 6 is therefore a tube, being the space bounded by helicoid capillary groove 14b on the surface of a cylindrical solid core and tube 14c closely fitting about said core.

Above the crystal retaining means 14 is a thermal sensing element 121 such as a thermocouple. The leads of the thermal sensing device 121 may be connected to a temperature recording device 122 and the bushing between the portions of the element 121 located inside or outside the measuring circuit hermetically seals the tube 13.

On the downstream side of the crystal retaining means 14, a pressure measuring tube 133 is connected to the differential pressure switch 125, the upstream side of the crystal retaining means is likewise provided with a pressure measuring tube 132.

A constant flow rate of the substance to be analyzed is provided at the inlet 140 which enables the continuous circulation of the substance in the metal tube 13. The continuous circulation in the analyzer apparatus causes a pressure drop in the circuit. Then the progressive lowering of the temperature due to the cooling unit brings the substance circulating in the measuring circuit to a temperature close to the value corresponding to the filterability point and causes the accumulation of microcrystals of paraffin in the crystal retaining means 14 and the rapid increase of the pressure drop in the measuring circuit 132–133.

An increase in the pressure drop to about 1400 millibars brings about the actuation of the differential pressure responsive means 125, i.e., the differential pressure responsive switch connected to the measuring circuit by means of inlet pressure tube 132 and outlet pressure tube 133 controls the starting of the reheating sequence applying a potential difference of 1.5 true volts to the terminals of the metal tube 13. The tube has a resistance of 0.05 ohm. The heating element constituted by the tube consumes 45 watts. The metal wall of the metal tube 13 heats up and enables the efficient melting of the microcrystals which were deposited in the crystal retaining means 14.

The pressure drop due to the reduction of the effective cross-section of the crystal retaining means caused by the crystallization of paraffin, for a constant flow rate, rapidly returns to the initial value and in the proximity thereof, viz., near 700 millibars, the differential pressure switch 125 brings the heating sequence to an end, thereby enabling a new cooling sequence to begin.

The cooling is effected by means of the cooling bath 136 which is adapted to remove calories from the substance to be analyzed while providing a moment of thermal inertia sufficiently large so as to eliminate the inevitable variations in temperature resulting from the on-and-off operation of the cooling unit.

The elimination of variations is brought about by means of the solid mass 135 of steel. The specific heat of the steel is about one-eighth the specific heat of an aqueous solution but its density which is about seven times greater gives for an equivalent volume a moment of thermal inertia substantially equal to that of a large liquid bath.

The cavity 113 is filled with a non-freezing liquid 136 with a view to ensuring that heat transfer between the low temperature source which is constituted by the metal mass 135 and the metal tube 13 immersed in the measuring well.

The temperature of the non-freezing liquid is intermediary regulated in the course of the sequence by the periodic reheating of the capillary tube while the temperature of the solid mass 135 is maintained at a constant temperature of −25° C by the thermostat of the cooling unit.

The thermocouple 121 which measures the filterability point temperature remains at the outlet end of the metal tube 13 beyond the crystal retaining means 14 and enables the continuous recordings of the changes of the temperature between the minima representing the variations of the filterability point P.F. and the maxima representing the maximum temperature reached for ensuring the complete melting MP of the microcrystals.

Figure 7:
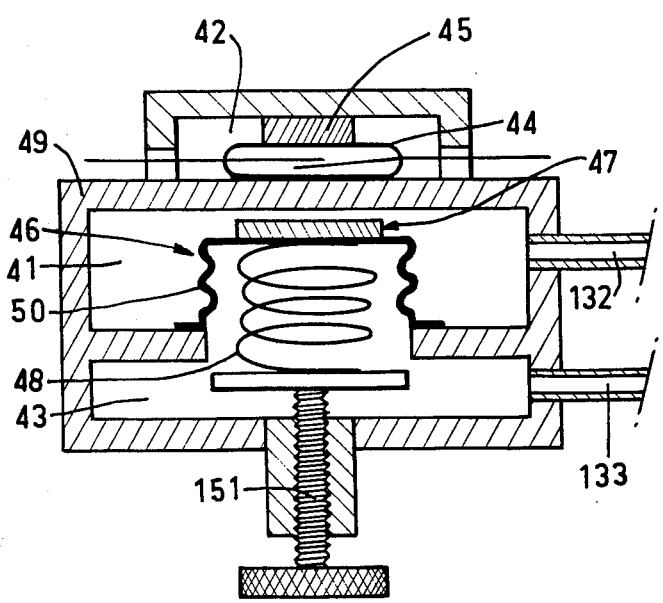
FIG. 7 is a schematic illustration of the differential pressure responsive switching means.

The differential pressure responsive switch illustrated in FIG. 7 includes three chambers 41, 42, 43. The inlet chamber 41 is joined to the high pressure connection 132. Chamber 41 is moreover in magnetic association with the switch chamber 42 by virtue of a magnet provided in each of these two chambers. The closed switch chamber 42 which is in adjacent superposition with respect to the chamber 41 houses both a magnetically responsive switch 44 connected to the power supply for the heating element 23 and a polarizing magnet 45. The chamber 41 includes scaled central cylindrical zone 46 which is defined by a bellows member 50 which supports on its top surface an actuator magnet 47 facing the adjacent wall 49 common to chambers 41 and 42. The inner side of the sealed cylindrical zone 46 is in communication with the outlet chamber 43. A coil spring 48 is provided in the sealed cylindrical zone between the underside of the top surface of the bellows 50 and an adjustment screw 151 with its knurled knob accessible to the outside. The outlet chamber 43 is connected to the low pressure connection 133.

The operation of the differential pressure switch will now be described.

As described above, the constant flow rate at the inlet of the crystal retaining means 14 causes a slight pressure drop in the measuring circuit. The progressive fall in the temperature due to the cooling system brings the diesel oil flowing through the crystal retaining means 14 to a temperature close to the filterability point and causes the accumulation of microcrystals of paraffin on the crystal retaining means 14 and the rapid increase in the pressure drop across the crystal retaining means 14. This increase in the pressure drop actuates the differential pressure responsive switch means at a pressure corresponding to that set.

Indeed, when there is an increase in the pressure drop, the pressure differential between the chambers 41 and 43 decreases which causes an expansion of the bellows 50 so that the actuator magnet 47 on the top surface of the bellows comes closer to the common wall 49 separating the chambers 41 and 42. The actuator magnet 47 of polarity opposite that of the magnet 45 is pulled farther towards the common wall thereby opening the switch magnetically, the switch being normally closed. The heating circuit is then supplied through a reversing relay now shown. The temperature in the measuring circuit then increases by the heating of the metal tube 13 thereby melting all the microcrystals of paraffin previously deposited on the crystal retaining means 14. The reheating causes the pressure drop across the crystal retaining means 14 to decrease. The pressure in the chamber 41 thus increases with respect to the chamber 43, and the bellows 50 contracts carrying with it the actuator magnet 47 away from the common wall 49 and the other magnet 45. The differential pressure switch is adjusted by means of the adjustment screw 151 effectively controlling the position of the actuator magnet 47 with respect to the common wall 49 of the chambers 41 and 42. This adjustment is made so that as soon as the value of ΔP is a little greater than the initial value, the distance between the two magnets 47, 45 corresponds to the point at which the magnet 45 causes the switch 44 to open. The power supply to the resistance heating of metal tube 13 is thus cut off.

A second sequence or cycle thus beings automatically and so on.

The analyzer of the invention demonstrates further advantageous characteristics. Indeed, for the preadjusted range of ΔP at the two sides of the crystal retaining means of about 700 millibars, the recorded temperature varies substantially between a minimum value $\Delta T_M$ of 2° to 3° C and a maximum value $\Delta T_M$ which may reach 15° to 20° C for the same filterability point. Now, since the maximum temperature attained for ensuring the melting of all the microcrystals and the return to the initial ΔP is variable according to the distillation cross-section representing the substance to be analyzed, the continuous recoring of the temperature of the substance leaving the tube allows not only the instantaneous value of the filterability point to be determined but also the quality of the cracking or fractional distillation in the cracking or distillation tower.

If the molecular weight of the crystallizable paraffins is relatively grouped, the difference between the melting points of the lightest and heaviest remains slight thereby proving a good fractional distillation. On the other hand, if the distillation tower operates improperly or if there is a breakdown, the molecular weight and melting temperature of the crystallizable paraffins are more scattered which is transcribed by the recording device as a rise in ΔT.

This phenomenon may be taken advantage of for using the data from the analyzer by transmitting it to the control system for the distillation tower in order to vary the parameters accordingly and thereby obtain a kind of self-regulation or feedback control.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. Apparatus for the continuous automatic measure of the filterability threshold temperature of a liquid substance comprising a container for a cooling liquid, a cooling liquid substantially filling said container, said cooling liquid having a freezing temperature substantially lower than the average filterability threshold temperature of the type of liquid to be analyzed, cooling means adapted to cool said cooling liquid, an electrically conductive metal tube immersed in said cooling liquid and having an inlet end and an outlet end emerging from said cooling liquid, said tube being electrically insulated, pump means for delivering the liquid to be analyzed to the inlet of said tube at a constant volume flow rate, a crystal retaining means at the outlet end of said tube emerging from said cooling liquid, electrical connecting means to connect both ends of said tube with the terminals of an electric power supply, respectively, switch means interposed on one of said electrical connecting means, pressure responsive means in connection with said switch means whereby said electric power is supplied to said electrically conductive metal tube when the difference between the pressure measured just before said crystal retaining means and the pressure measured just beyond said crystal retaining means exceeds a first predetermined value and suspends said supply of electric power when said pressure difference reaches a second predetermined value lower than said first value, thermosensitive means adapted to measure the temperature of the liquid to be analyzed just beyond said crystal retaining means, and means for recording the temperature measured by said thermosensitive means.

2. The apparatus of claim 1 wherein said crystal retaining means is a fine meshed sieve.

3. The apparatus of claim 1 wherein said crystal retaining means is a helicoid capillary tube.

4. The apparatus of claim 3 wherein the helicoid capillary groove is
the space bounded by a helocoid capillary groove on the surface of a cylindrical solid core and a tube closely fitting about said core.

5. The apparatus of claim 1 wherein said container for a cooling liquid is a block of metal having a high thermal inertia, said block of metal having a closed recess therein forming said container and said cooling means adapted to cool said cooling liquid is said block of metal having a cooling means on the external surface of said block.

6. The apparatus of claim 1 wherein the thermosensitive element is a thermocouple.

7. The apparatus of claim 1 wherein the thermosensitive element is a thermistor.

8. The apparatus of claim 1, further comprising a memory device associated with said recording means enabling the continuous recording of only the outline of the recording curve connecting the points corresponding to the minimum temperatures recorded, i.e., instantaneous filterability points.

9. A process for the continuous automatic measure of the filterability threshold temperature of a liquid substance consisting essentially of the steps of pumping a liquid substance to be analyzed at a constant volume flow rate through an electrically conductive metal tube immersed in a cooling liquid having a freezing temperature substantially lower than the average filterability threshold temperature of said liquid substance to be analyzed, said metal tube being electrically insulated, passing said liquid substance from said tube through a crystal retaining means situated beyond said cooling liquid, measuring the pressure differential between both sides of said crystal retaining means, applying a supply of electrical power through said electrically conductive metal tube when the measured pressure differential exceeds a predetermined value, whereby said liquid substance is heated, and constantly measuring the temperature of said liquid substance at the outlet side of said crystal retaining means.

10. The process of claim 9 wherein said crystal retaining means is a fine meshed sieve.

11. The process of claim 9 wherein said crystal retaining means is a helicoid capillary tube.

* * * * *